United States Patent [19]

Wiech, Jr.

[11] Patent Number: 4,858,324

[45] Date of Patent: Aug. 22, 1989

[54] KNIFE BLADES AND METHOD OF MAKING SAID KNIFE BLADES

[75] Inventor: Raymond E. Wiech, Jr., San Diego, Calif.

[73] Assignee: Edge Engineering, Inc., San Diego, Calif.

[21] Appl. No.: 937,480

[22] Filed: Dec. 3, 1986

Related U.S. Application Data

[63] Continuation of Ser. No. 569,960, Jan. 11, 1984, abandoned.

[51] Int. Cl.⁴ ............................................. B26B 9/02
[52] U.S. Cl. ...................................... 30/357; 30/355; 128/305
[58] Field of Search ..................... 30/357, 123, 355; 128/303.14, 305; 76/101 A, 101 R

[56] References Cited

U.S. PATENT DOCUMENTS

| | | | |
|---|---|---|---|
| 3,597,844 | 8/1971 | Messinger | 30/246.53 |
| 3,786,814 | 1/1974 | Armao | 128/305 X |
| 4,016,761 | 4/1977 | Rozzell et al. | 128/736 X |
| 4,248,231 | 2/1981 | Henczog et al. | 128/303.14 |
| 4,253,469 | 3/1981 | Aslan | 128/736 X |
| 4,402,311 | 9/1983 | Hattori | 128/736 X |
| 4,502,487 | 3/1985 | DuBrucq et al. | 128/736 X |

OTHER PUBLICATIONS

Tamura et al., "Noncontact Transducer for Monitoring Blood Temperature During Extracorporeal Circulation", published in 'Medical Instrumentation', vol. 14, No. 2, Mar. 1980, pp. 107–110.

*Primary Examiner*—Frank T. Yost
*Assistant Examiner*—Willmon Fridie, Jr.
*Attorney, Agent, or Firm*—Jay M. Cantor

[57] ABSTRACT

The disclosure relates to knife blades for precision cutting, such as in optical surgery, wherein the blade or cutting edge is formed from a molded plastic filled with particulate material which is much harder than the plastic, the particles of particulate material being generally smaller in their largest dimension than the radius of curvature of the apex of the cutting edge. A thin coating of a metal which is much harder than the filled plastic is coated onto the cutting edge to replicate the molded shape and provide substantial additional hardness to the blade edge. In a further embodiment, a transducer is molded into the blade body adjacent the edge with all processing steps being at temperatures below those harmful to the transducer. Another embodiment provides light conducting elements molded into the blade body for measurement of cut depth or the like. A further embodiment provides capillary tubes from the blade interior to its surface with provision for transmission of fluid under pressure from the blade interior to the surface. A still further embodiment provides a wire molded into the blade body and contacting the metal coating at or near the blade edge to form a thermocouple therewith for temperature measurement.

20 Claims, 3 Drawing Sheets

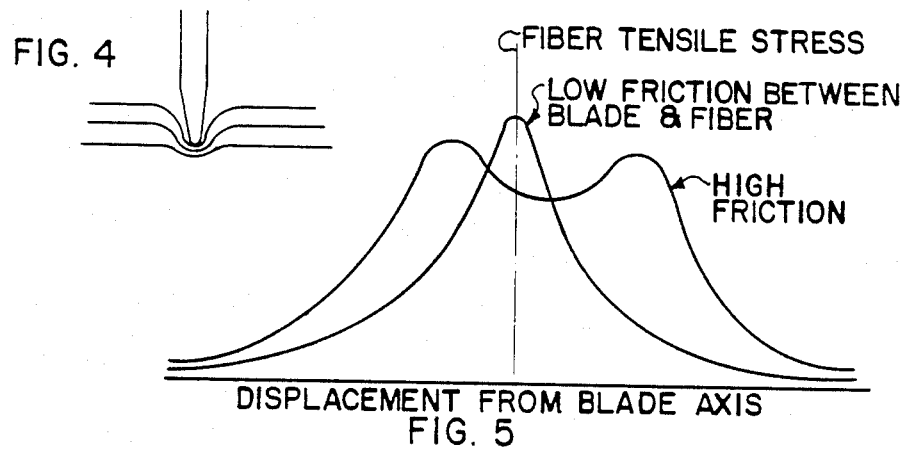
FIG. 4
FIG. 5
FIBER TENSILE STRESS
LOW FRICTION BETWEEN BLADE & FIBER
HIGH FRICTION
DISPLACEMENT FROM BLADE AXIS
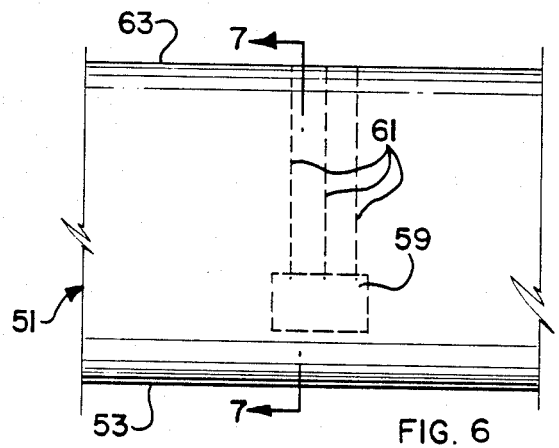
FIG. 6
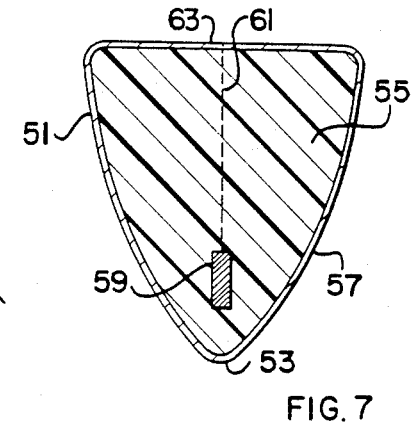
FIG. 7
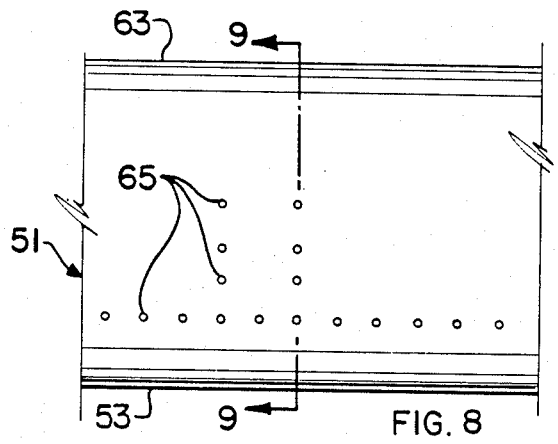
FIG. 8
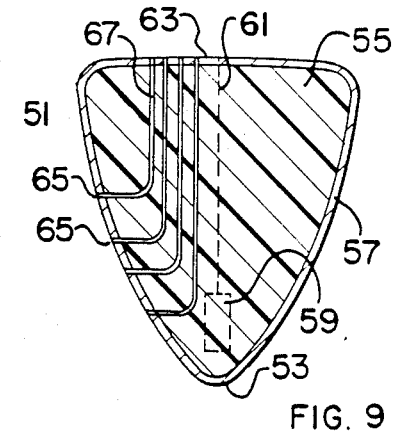
FIG. 9

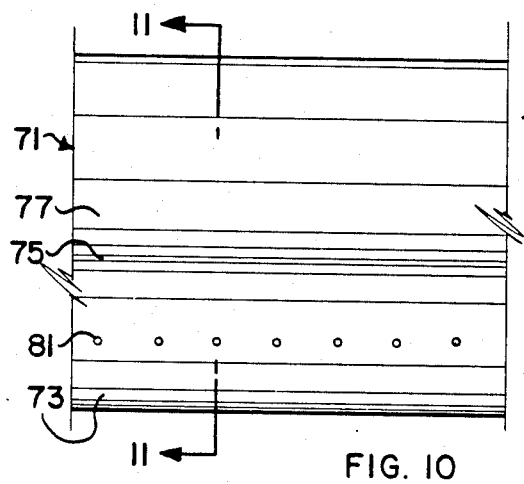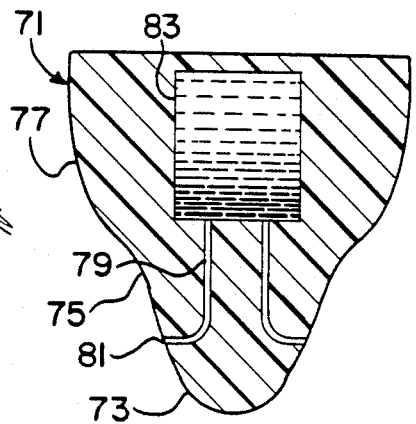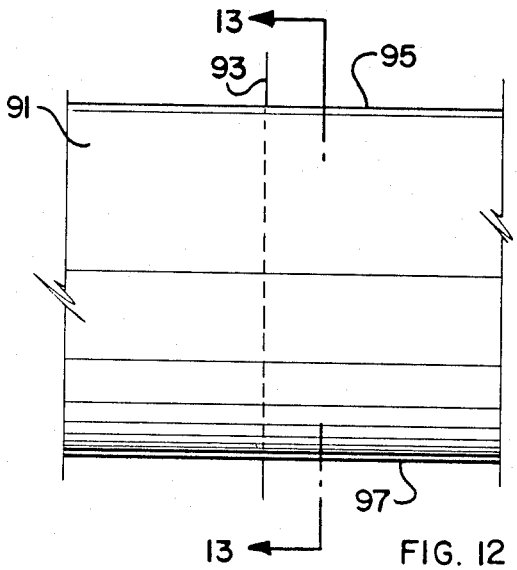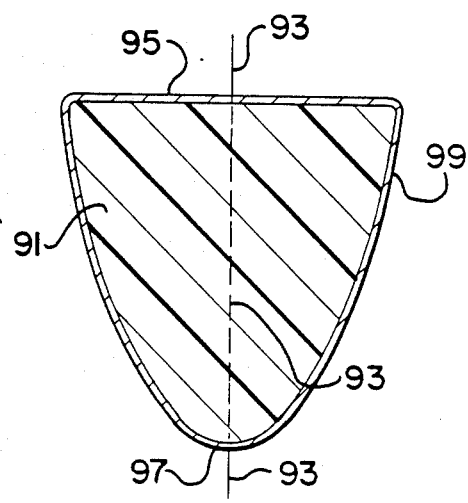

KNIFE BLADES AND METHOD OF MAKING SAID KNIFE BLADES

This application is a continuation of application Ser. No. 569,960, filed Jan. 11, 1984 now abandoned.

BACKGROUND OF THE INVENTION

1. FIELD OF THE INVENTION

This invention relates to knife blades and method of making said knife blades.

2. DESCRIPTION OF THE PRIOR ART

Conventional knife blade manufacture has produced cutting edges from prehistoric times by substantially the same process steps, these being (1) select blade material to be as hard as possible for the job, (2) form the blade by some mechanical means, such as machining, chipping, etc., (3) if not already hardened then harden, and (4) establish fine edge by lapping, honing, sharpening, etc.

In general, the harder, smoother and sharper (smaller blade tip radius) the blade is, the better the cutting properties. Frequently, because hardness and ductility are generally inverse material properties, materials that are less than full-hard are used to provide toughness to the blade. Much of the mystique and lore of knives is built around the opposite requirements of blade hardness and blade toughness, especially in weapons. Many of the secrets of superior blade manufacture revolve about this set of antagonistic requirements.

Historically, fine blades have been made one at a time. They have been the subject of a great deal of individual effort. Even production knives are produced individually. Substantially, the only cutting edge that is produced on a continuous production process basis is the safety razor blade. The quality of a blade strictly depends upon the craftsman producing the blade. The edge is developed by personal skill of the craftsman producing the edge. Even in the case of razor blades, the set-up and maintenance of the production equipment requires a great deal of individual skill. In terms of specifications, as normally found in most technological production items, the production blade is purchased or sold primarily on the basis of reputation of the manufacturer. The parameters of cutting or slicing are not really specified and skilled users of knives, such as surgeons, do not procure their instruments by specification of the edge. Knives costing thousands of dollars are purchased by reputation of the manufacturer, not by specifying the edge.

In addition to the lack of specifications, the user of the blade is limited by his personal skills and craftsmanship as to the quality of the slice that is being taken. The depth, temperature of the ambient environment, the resistance to slicing of the matter being sliced, etc., are all highly subjective and dependent upon the skills of the user. The ability to instrument and place within the blade structure itself transducers that can monitor and/or control the blade function on an objective basis is a highly desirable feature. For example, surgeons currently operate without precise knowledge of the conditions that exist at the edge of the blade they are using. For example, diseased tissue is frequently associated with being at a temperature that is higher than healthy tissue. A blade that incorporates a sensitive temperature transducer within the blade and at the edge thereof, would provide the surgeon with an objective insight as to the conditions that exist at the precise location of the slice. This has not been possible in the past because of the construction technique of blade manufacture.

SUMMARY OF THE INVENTION

In accordance with the present invention there is provided a method of producing a knife blade by replication and process techniques so that blades of consistent performance can be manufactured by process in multiples rather than individually and where the skill of the craftsman is not a factor in producing the blade and edge. The blades and edges are produced by physical and geometrical specification, such as size and shape of the edge and at modest temperatures so that various sensors, transducers and ancillary devices can be incorporated into the blade body during construction or production thereof.

A survey of scientific and technological literature provides very little information and insight into the rather fundamental question of what constitutes a good knife cutting edge. The following is a summary of the literature noted as well as my own concepts of the theory of blade or knife edge operation.

The action of cutting any material requires several things to occur. This discussion will be oriented toward biological material or surgical cutting, carving, dissection, shearing, slicing, etc. However, it should be understood that it is not limited to this area, but is quite general. Cutting can be divided into two distinct phenomena:

1. The normal force of the blade against the tissue causes forces that exceed the tensile strength of the tissue and severs the tissue. The tensile stress of the tissue at the blade edge exceeds the tensile strength of the tissue and the tissue mechanically fails. This will be called the severing phase.
2. The severed tissue is forced along the side of the blade. The normal force of the tissue against the blade causes drag or resistance to further severing. The drag force acts in the opposite direction to the severing force and reduces the available severing force from the total applied cutting force. This will be called the dividing phase.

If the forces acting during cutting are examined, a very complex set of relationships is found to exist. Due to the highly variable structures found in biological systems, approximative relationships will first be established to explore the mechanisms involved. FIG. 1 shows a highly simplified knife blade schematically during the act of cutting. The blade edge has a radius "R" and is shown being forced against several fibers with a force "F". The bottom unstressed fiber has an initial tension "$T_0$", which is characteristic of all biological fibers in vivo (i.e., living tissue has the characteristic of being under tension to "hold things together"). Succeeding fibers above the unstressed fiber are placed in succeeding states of increased tension so that $T_0 < T_1 < T_2$.

When the mechanics of this system are examined, it is apparent that an interaction exists between the fibers such that the tension is shared between them to reduce the forces in the neighborhood of the blade edge. These interrelationships between the fibers will be ignored because the results will not be qualitatively changed. FIG. 2 shows the basic forces that exist at the blade edge. Again, a simplification will be assumed here. The fiber/blade interaction is frictionless, i.e., tension in the fiber is uniform throughout its length.

The only mechanism present to separate the fiber is that it must fail in tension, i.e., the tensile stress exceeds the tensile strength of the fiber. The force diagram of FIG. 2 under these conditions shows that the tensile stress in the fiber is given by:

$$T = T_0 + F/2 \mathrm{Sin}(\Phi)$$

There is no physical process under these idealized one-dimensional conditions that will cause the fiber to separate specifically under the blade edge. The sole criterion of separation is that the tension in the fiber exceeds the ultimate tensile strength of the fiber. As this condition can exist (under these idealized one-dimensional conditions) throughout the length of the fiber, there is no special set of conditions that exists at the edge that will cause the one-dimensional frictionless fiber to part at the edge. The effect of additional fibers must therefore be considered. FIG. 3 shows the effect when there are a number of connected fibers at the blade edge. FIG. 4 shows an enlarged view of the overall blade. In this case it is seen that the fiber closest to the edge is the fiber that has been elongated the most. Each fiber beneath the fiber closest to the edge is connected to the outer fibers and they take up part of the stress. The exact relationship is very complex but, to a first approximation, the stress in the fiber next to the blade tip at the tip axis is:

$$T = f(F/R)$$

where f( ) is a generalized functional relationship that is not specifically known.

The tension in the closest fiber is a complex function of the normal force on the blade directed into the tissue and inversely proportional to the radius of the blade tip. Again, the assumption here is that of a frictionless surface but the tension maximizes at the tip axis as there is no available stress component there to diminish the tension. Infinitessimally from the axis the fibers spatially diverge, making available components of stress to share in the fiber stress.

Friction between the closest fiber and the blade tip complicates the picture. Friction components can share in the closest fiber stress and, depending upon the coefficient of friction, can result in maximum tension in the closest fiber that is displaced from the axis. This results in a pair of maximum tension points in the closest fiber that are displaced from the axis of the blade. The practical result is that a slice taken by a high-friction edge will oscillate between the high stress lobes and the slice will be formed by a tearing action rather than a clean separation of the singular value of maximum stress of the low friction condition. In the highly complex conditions that exist at the blade edge, there may be a multiplicity of high tension values so that the tearing condition can be spread through a region.

The criterion for cutting is that the closest fiber must ultimately part, and this will occur when the fiber tension exceeds the strength of the fiber. The blade edge must not yield beyond some minimum value under the stresses involved as the blade tip width will increase. The size and friction existing at the edge should be such that the slice will be clean and single-valued. This is especially important in surgical procedures as trauma is minimized as the slice becomes cleaner (single-valued with no friction).

Once the fibers are severed they will contract and be forced up the blade side. Frictional effects will reduce the normal cutting force and will manifest itself as drag. To minimize drag and maximize the true normal force at the tip the fibers must be removed from the blade edge in as short a distance as possible once they have been severed.

The manufacturing technology of injection molding of plastics has proven itself to be capable of replicating a mold cavity virtually exactly in a highly economic, repeatable and reliable manner. Dimensions of less than one micron are regularly reproduced by injection molding in the manufacture of laser video discs, video discs, and phonograph records. That the injection molding technology is capable of virtually exact replication of the surface of mold cavities is not a question here, it is a statement of fact.

The technological ability to replicate a blade in plastic by the techniques well known to mold makers and molders can be assumed to be state-of-the-art. However, a plastic blade, no matter how well replicated, will not serve as a superior cutting edge. In accordance with the present invention, there is provided an injection molded blade superior to prior art blades, reproducable, economic and primarily for medical surgery, though not limited to that use.

The requirement of high apparent hardness at the blade edge for an effective blade means that if a blade (with its edge) is to be formed by injection molding of plastic materials, then a method of providing the blade with a high apparent hardness must be found. This invention provides a method of producing a blade that is formed by plastic injection molding at conventional plastic flow temperatures that has the necessary apparent hardness for use as a surgical blade.

The requirement that the plastic replicate the mold to create the desired blade and edge dictates that the plastic must flow essentially as a liquid during the molding cycle. The closeness with which the plastic must behave as a liquid depends to some extent upon the smallest dimension that must be replicated. For example, if the desired edge is to have a diameter (width) of one micron, then the plastic must act as a liquid over dimensions that are less than one micron. Exactly how much less is a function of the other process parameters.

Once the blade has been molded and allowed to harden, either by cooling, chemical reaction, or a combination thereof, the blade surface must be provided with an adherent coating of high hardness that replicates the injection molded substrate. This provides the surface of the blade with the high hardness necessary for use. Although these steps are necessary, they will not provide in themselves the necessary conditions for a successful blade unless other conditions are met.

An effect, known as the anvil effect, states that a thin layer of a material placed in inimate contact with a heavy substrate will reflect, to some extent, the properties of the substrate. Thus, a thin layer of rubber placed on a steel anvil will reflect the properties of the anvil. When struck with a hammer, the rubber will appear to be much harder than it really is. A steel sheet on a rubber anvil will appear to be softer than it actually is when struck with a hammer.

Thus, a thin hard coating on a relatively soft plastic substrate will reflect the characteristics of the substrate. Simply placing a hard coating on a molded plastic blade will not provide the necessary characteristics to make an acceptable blade. The nature of the plastic must be altered to increase its apparent modulus of elasticity so that it is far more rigid than it is in its virgin state. This may be accomplished by adding solid particulate material to the plastic to form a plastisol (which is defined here as a suspension of finely divided particles in a continuous plastic matrix).

The apparent modulus of elasticity of a filled plastic is given by the relationship:

$$M_a = M_p \times g\,(1 - V/V_m)$$

Where
  $M_a$ = Apparent modulus
  $M_p$ = Modulus of virgin plastic
  $g(\ )$ = Functional relationship
  $V$ = Actual volume fraction of solids
  $V_m$ = Maximum possible volume fraction of solids The apparent modulus has as its end point the modulus of the solid particles and the functional relationship is to a negative power greater than two over much of the relationship so that the apparent modulus rapidly increases as the solids volume fraction is increased. Thus a high volume fraction of solids is indicated. A volume fraction that is nearly at the maximum volume fraction that the plastisol can have is preferred. If the dispersed solid particles are spheres all of the same diameter, then the maximum volume fraction of solids in the plastisol is about 63%. If the solid particles are of several different diameters (or are continuously graded) so that the smaller particles can fit between the larger ones, the maximum volume fraction is increased to over 63%. Applicant has produced plastisols that have a reasonable viscosity which have solid volume fractions of over 85%.

Typical values of the modulus of elasticity for virgin plastics are on the order of several hundred thousand pounds/square inch. When typical plastics are loaded to high volume fractions that are close to their maximum volume loadings for the particular particles being loaded into the plastic to form the plastisol, the apparent modulus can be increased to values on the order of several million pounds/square inch. This is a modulus that is about that of magnesium and provides the rigidity necessary to support a hard coating effectively.

The use of fine particles to increase the apparent modulus of the plastic is actually a form of dispersion hardening. The maximum particle size employed must be smaller than the smallest dimension desired to be replicated if maximum effectiveness of the hardening on a microstructure basis is to be obtained. The objective is to have as many particles near to the surface of the molded article as possible to minimize the amount of plastic matrix at the surface. Fine particles tend to agglomerate and care must be taken to insure that the agglomerates are broken up and only the individual dispersed particles become part of the plastisol.

Thus, by highly volume loading a well dispersed population of fine articles into a plastic matrix to a volume loading close to, but not exceeding, the maximum volume loading possible, a moldable blade substrate material of acceptable properties is produced.

The next process step to consider is the production of the hard surface coating of the molded blade substrate. Any method of producing a hard, adherent, conformal coating that is chemically compatible with the intended application is acceptable. However, to be specific, one method will be discussed in detail, that of electroless plating.

Electroless plating coatings are uniform, regardless of the geometry of the substrate and thereby the interior and exterior surfaces of the coating replicates the cutting edge of the body. They are hard, and they show excellent corrosion resistance. Electroless nickel is biocompatible. Its hardness and inertness can be increased by modest heat treating at a relatively low temperature. The development of acceptable formulations of materials such as ABS (acrylonitrile-butadiene-styrene) and other plastics, and of chemical etchants capable of producing a controlled microporous surface, permits plastics to be plated with a combined mechanical and chemical bonding of the plated layer to the surface of the substrate. While the most popular substrate plastic for plating applications is ABS, other plastics such as phenylene oxide, filled polypropylene, filled nylons, polysulfone, urea formaldehyde, and others, can be used as acceptable plating substrates.

For the best replication of minute dimensions, amorphous (non-crystalline) plastics are preferred. Thus, a highly filled (almost to the point of non-flow) amorphous plastic material which has good high temperature stability during processing and which will accept an adherent electroless nickel plate is desired. The sulfone polymers, for example, have properties that meet these general criteria.

Since a utilitarian device such as a cutting edge can be produced as described hereinabove without the requirement of a processing step utilizing temperatures incompatible with semiconductor devices, it is possible to insert semiconductor devices, such as transducers, integrated circuits and the like into the forming device prior to device formation. The utilitarian device thereby acts both in the capacity for which it is intended as well as a packaging for the seimconductor device itself. Therefore, in the case of the above described knife, an insert holding the semiconductor device or chip is placed into the mold at the desired location (preferably as close as possible to the cutting edge) with wires extending outwardly therefrom for later external connection with subsequent molding and processing taking place in the manner described hereinabove. The wires are subsequently connected to external elements in known manner. In this way, parameters such as temperature, etc. at the knife edge can be determined on-line. Other types of transducers or other devices can be used to replace the semiconductor device.

A further embodiment, formed either in conjunction with the above described encased semiconductor device or alone includes the insertion of light conducting elements into the mold which are held in position by an appropriate mold insert. The light conducting elements are preferably in the form of fibers and extend out of the mold cavity in the direction away from the knife edge in the case of such embodiment. The other ends of the light conducting elements extend through what would be the knife side wall with subsequent molding and processing taking place as noted hereinabove. The portion of each light conducting element extending through the knife side wall is then lapped back to remove any plated region on the edge thereof.

A still further embodiment of the invention includes shaping the region at the knife edge whereby the cross-section is narrow with some taper for a short region and then the degree of taper rapidly increases so that fibers or the like that have been cut will initially be pulled away from the knife edge and not drag thereon. Apertures extending through the utilitarian device interior terminate at the region of narrow cross-section whereby a fluid under pressure is passed through said apertures and is expelled at said narrow region to provide a bearing-type surface for the cut fibers as they pass along the knife edge to reduce trauma. The apertures are formed by placement of appropriate inserts in the mold in known manner. The apertures can be replaced by capillary tubes inserted into the mold prior to the molding operation. The viscous forces in the capillary regulate the flow of fluid therethrough, thereby providing a dose regulating device in the structure. The fluid is applied to the aperture or the capillary tube under pressure. This pressure aids in separation of, for example, tissue during surgery since fluid flow will cease momentarily when the apertures are covered by tissue. However, the pressure will force the tissue away from the knife surface. The fluid can be contained in the utilitarian device under pressure or with a pressure source within a bladder and sealed therein. Removal of the seal causes the fluid under pressure to move through the apertures or capillaries.

BRIEF DESCRIPTION OF THE DRAWINGS

FIG. 4 is a view as in FIG. 3 but of a longer area;

FIG. 5 is a diagram of the relative tension in the closest fiber to the blade edge of FIG. 3 as a function of friction between the fiber and the distance from the blade centerline;

FIG. 6 is a schematic diagram of a blade in accordance with the present invention having a transducer encased therein;

FIG. 7 is a view taken along the line 6—6 of FIG. 6;

FIG. 8 is a schematic diagram of a blade in accordance with the present invention having fiber optics contained therein;

FIG. 9 is a view taken along the line 9—9 of FIG. 8;

FIG. 10 is a schematic view of a blade in accordance with a further embodiment of the invention with provision for dispensing a fluid therethrough;

FIG. 11 is a view taken along the line 11—11 of FIG. 10;

FIG. 12 is a schematic view of a blade wherein a thermocouple is formed at the cutting edge between a wire and the blade coating; and FIG. 13 is a view taken along the line 13—13 of FIG. 12.

DESCRIPTION OF THE PREFERRED EMBODIMENT

Figure 1:
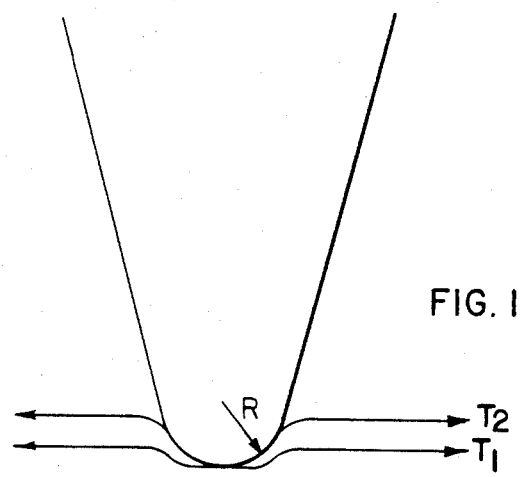
FIG. 1 is a schematic diagram of a knife blade edge during a cutting operation.
Figure 2:
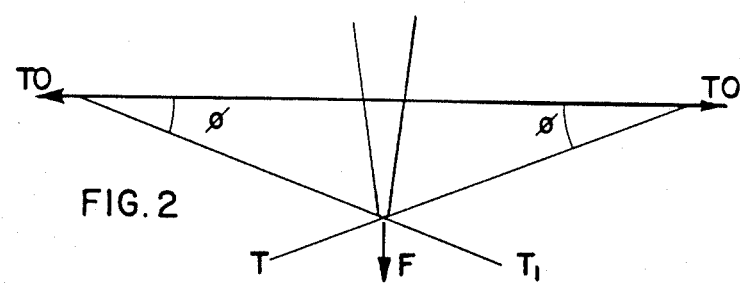
FIG. 2 is a diagram of the forces that exist at the blade edge.
Figure 3:
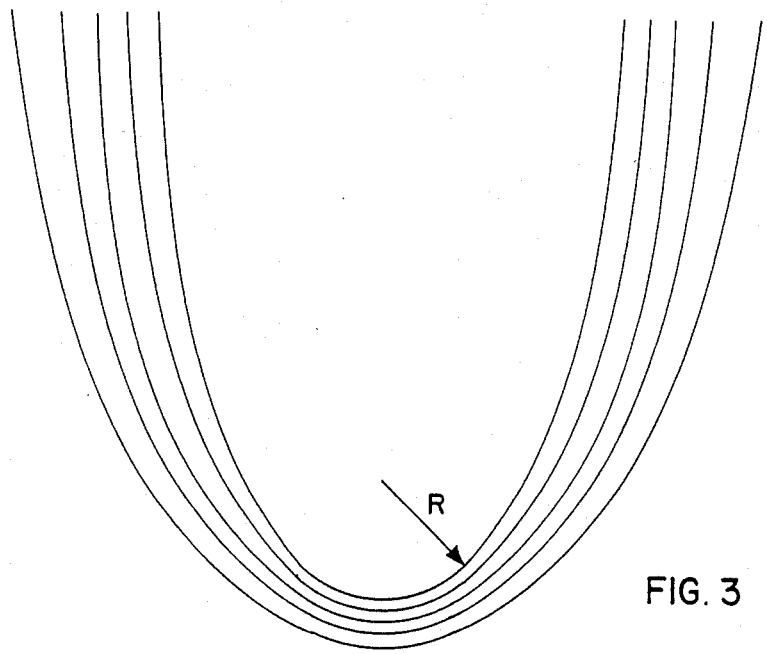
FIG. 3 is a schematic diagram of a knife blade edge cutting through several connected fibers.

The manufacture of utilitarian devices of the type above described and the devices themselves will be described specifically with reference to surgical knives, particularly those used for eye surgery. However, it should be understood that the principles herein have wide application in other areas and that the invention herein is not limited to the preferred embodiments described.

The following are an example of the manufacture of a surgical knife used for eye surgery:

EXAMPLE 1

A mold of a knife blade was made and injection molded from ABS (Borg Warner type EP-3510) which had been loaded with 55% by volume of 0.3 micron (0.7 to 0.1 micron range) alumina powder ALCOA type A-16) by hot mixing and dispersing the alumina into the ABS. The mixing and dispersion of the alumina into the ABS was accomplished by conventional technique that is employed by the plastics industry to produce "filled plastics". The blade was microscopically examined to insure that the edge in the mold was replicated.

An etch bath of 3.5 pounds per gallon of chromic acid plus 20% by volume of concentrated sulphuric acid and 9% by volume of a commercial wetting agent/etch aid manufactured by Enthone Corporation and sold as Enplate Q519 was made in a lead-lined tank. The acid solution was heated to 160° F. and the molded blade placed in the hot acid for 15 minutes. The etched blade was removed from the acid bath and rinsed in running tap water three (3) times and then placed in a neutralizing bath of 4% Enthone PA 492 with 10% HCl by volume at 120° F. for five minutes. The blade was removed from this solution and rinsed in running tap water three (3) times.

Next, the blade was placed in a 25% by volume solution of reagent grade HCl at 80° F. for one minute. The blade was then placed into a catalyst bath solution of 25% by volume of reagent grade HCl plus half percent by volume of Enplate 443 (a tin complex) at 80° F. for five minutes. The blade was then removed from this solution and was given two (2) rinses in running tap water.

The blade was next transferred to an accelerator solution of 4% by volume of Enplate PA492 plus 2.5% by volume of $H_2SO_4$ reagent grade in re-ionized water at 140° F. for 90 seconds. The blade was removed from the solution and given two (2) rinses in running tap water.

The blade was then transferred to a solution of Enplate Cu750 (an electroless copper plating solution) at 80° F. for two minutes to provide a copper flash of approximately 2 microinches thickness. The blade was then transferred to a low phosphorous electroless nickel plate solution (Enplate Ni 8632) at a temperature of 180° F. for one hour.

The blade was removed from the bath and rinsed clean. The blade was tested by examination under a microscope and appeared to replicate the mold. The blade also appeared to cut tissue without excessive drag.

EXAMPLE 2

A mold of a knife blade was made as in Example 1 except that a mold insert was provided in the mold holding a semiconductor temperature transducer with wires bonded to the pads thereon and extending out of the mold in a direction away from the blade edge at a location closely adjacent the blade edge. The procedure and materials of Example 1 were then utilized. The end result was a knife blade which performed the dual function of encasing a semiconductor transducer therein and operating as a knife.

The knife blade produced by the process of Example 2 is shown in FIGS. 6 and 7 wherein the blade portion 51 tapers to the blade edge 53. The body of the blade includes the filled plastic portions 55 and the hard coating 57 thereon. Encapsulated within the blade is a semiconductor temperature transducer 59 with leads 61 extending from pads on the transducer 59 to the upper surface 63 of the blade. Connection is made to the leads 61 by an external device for use of the signal from transducer 59 in known manner.

EXAMPLE 3

A mold of a knife blade was made as in Example 2 except that the mold insert also supported a plurality of one millimeter diameter optical fibers which extended outwardly through apertures formed in the portion of the mold forming the blade sides. The other ends of the fibers extended out of the mold along with the wires. The procedure and materials as set forth in Example 1 were then utilize to form the knife blade as in Example 2 but with portions of the light fibers extending from the blade sides. The fibers were mechanically lapped back to the blade surface to also remove the coating from the edges thereof.

The knife blade produced by the process of Example 3 is shown in FIGS. 8 and 9 wherein the blade portion 51 further includes the ends of light conducting rods 65 extending through a side thereof and the blade portion body to the upper surface 63. Light is transmitted along the rods 67 to their ends 65 and is reflected therein in a manner whereby depth, etc. can be measured in well known manner in accordance with the reflections from the several rods which are arranged in a matrix array as shown. This example can also be produced without the transducer.

EXAMPLE 4

A mold of a knife blade was made as in Example 1 with a shape as shown in FIGS. 10 and 11. A plurality of capillary tubes and a fluid chamber connected thereto were positioned in the mold in standard manner using a mold insert and the blade was then molded using the procedures and materials as set forth in Example 1. The end result was a knife with apertures at the sides of the cutting region which extended into the blade body to a fluid source.

The knife blade produced by the process of Example 4 is shown in FIGS. 10 and 11. The blade includes a body portion 71 and metallic coating (not shown) as in FIGS. 7 and 9. The external contour of the blade has a concave outward portion 73, followed by a concave inward portion 75 followed by a further concave outward portion 77. The cutting region is primarily at the portion 73. Capillary tubes 79 within the blade body 71 extend to apertures 81 at the blade surface in the region 73 though these apertures could also be disposed in the region 75 or in both regions 73 and 75. The tubes 79 also extend to a fluid and pressure source 83 which can be within the blade during molding as shown or which can be external to the blade and connected directly to the capillary tubes 79. Pressure is applied within the pressure source 83 preferably by breaking a bladder to release the pressure at the source 83 and force the fluid through the capillaries 79. In this way, the fluid released at apertures 81 will form a bearing surface between tissue and the knife blade after severing of tissue and decrease trauma.

EXAMPLE 5

A mold of a knife blade was made as in Example 1 and a one mil wire formed of chromel (though alumel and other appropriate metals could be used which form a thermocouple with the metal plated on subsequently) was positioned to extend from the back portion of the blade through the blade surface at the cutting edge (the wire can exit the blade slightly offset from the blade edge, if desire). The blade was then molded around the wire using the procedure as set forth in Example 1. The end result was a knife blade wherein a thermocouple was formed at the junction of the wire and the plated region.

The knife blade produced by the process of Example 5 is shown in FIGS. 12 and 13 wherein the blade body 91 has the above described wire 93 extending therethrough from the blade back edge 95 through the cutting edge 97. The plated surface 99 is in electrical contact with the wire 93 at the cutting edge 97 only to form a thermocouple at the cutting edge. After removal of the knife blade from the mold, the portion of the wire 93 extending beyond the blade surface at the cutting edge was lapped back to the cutting edge surface and was flush therewith. Connection from electrical measuring equipment is made to the part of wire 93 extending through the back of the knife and to the coating 99 between which the generated voltage is measured.

Though the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

What is claimed is:

1. A method of forming a cutting edge comprising the steps of:
    (a) providing a settable moldable material;
    (b) providing a mold;
    (c) molding said moldable material in said mold in the shape of a pair of surface meeting along a line to form a cutting edge along said line;
    (d) allowing the molded material to set;
    (e) providing a material which is hard relative to said set material; and
    (f) replicating the shape of said cutting edge with a continuous coating of said material of step (e) disposed over said cutting edge.

2. The method according to claim 1 wherein said step of providing a settable moldable material includes providing a moldable material which is a plastic containing fine particles of a material substantially harder than said plastic embedded therein.

3. The method according to claim 1 wherein said step of coating comprises electrolessly coating a metal onto said set molded material.

4. The method according to claim 2 wherein said step of coating comprises electrolessly coating a metal onto said set molded material.

5. The method according to claim 1 further including the step of disposing a transducer in said mold adjacent the cutting edge to be formed prior to molding said moldable material in said mold.

6. The method according to claim 2 further including the step of disposing a transducer in said mold adjacent the cutting edge to be formed prior to molding said moldable material in said mold.

7. The method according to claim 3 further including the step of disposing a transducer in said mold adjacent the cutting edge to be formed prior to molding said moldable material in said mold.

8. The method according to claim 4 further including the step of disposing a transducer in said mold adjacent the cutting edge to be formed prior to molding said moldable material in said mold.

9. The method according to claim 1 further including the step of disposing optically conductive means in said mold extending to two spaced locations within said mold prior to molding said moldable material in said mold.

10. The method according to claim 2 further including the step of disposing optically conductive means in said mold extending to two spaced surface locations within said mold prior to molding said moldable material in said mold.

11. The method according to claim 3 further including the step of disposing optically conductive means in said mold extending to two spaced surface locations within said mold prior to molding said moldable material in said mold.

12. The method according to claim 4 further including the step of disposing optically conductive means in said mold extending to two spaced surface locations within said mold prior to molding said moldable material in said mold.

13. The method according to claim 5 further including the step of disposing optically conductive means in said mold extending to two spaced surface locations within said mold prior to molding said moldable material in said mold.

14. The method according to claim 6 further including the step of disposing optically conductive means in said mold extending to two spaced surface locations within said mold prior to molding said moldable material in said mold.

15. The method according to claim 6 further including the step of disposing optically conductive means in said mold extending to two spaced surface locations within said mold prior to molding said moldable material in said mold.

16. The method according to claim 8 further including the step of disposing optically conductive means in said mold extending to two spaced surface locations within said mold prior to molding said moldable material in said mold.

17. A method of forming a cutting edge comprising the steps of:
    (a) providing a moldable material;
    (b) providing a mold;
    (c) molding said moldable material in said mold in the shape of a pair of surfaces meeting along a line to form a cutting edge along said line;
    (d) providing a material which is hard relative to said molded material in step (c); and
    (e) replicating the shape of said cutting edge with a continuous coating of said material of step (d) disposed over said cutting edge.

18. The method according to claim 17 wherein said step of providing a moldable material includes providing a moldable material which is a plastic containing fine particles of a material substantially harder than said plastic embedded therein.

19. The method according to claim 17 further including the step of disposing a transducer in said mold adjacent the cutting edge to be formed prior to molding said moldable material in said mold.

20. The method according to claim 17 further including the step of disposing optically conductive means in said mold extending to two spaced surface locations within said mold prior to molding said moldable material in said mold.

* * * * *